(12) United States Patent
Fukuda

(10) Patent No.: US 12,011,309 B2
(45) Date of Patent: Jun. 18, 2024

(54) IMAGE PROCESSING DEVICE, RADIOGRAPHY SYSTEM, IMAGE PROCESSING METHOD, AND IMAGE PROCESSING PROGRAM

(71) Applicant: FUJIFILM CORPORATION, Tokyo (JP)

(72) Inventor: Wataru Fukuda, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 288 days.

(21) Appl. No.: 17/694,614

(22) Filed: Mar. 14, 2022

(65) Prior Publication Data

US 2022/0304647 A1 Sep. 29, 2022

(30) Foreign Application Priority Data

Mar. 24, 2021 (JP) ................................. 2021-050391

(51) Int. Cl.
*A61B 6/00* (2006.01)
*A61B 6/02* (2006.01)
*A61B 6/50* (2024.01)

(52) U.S. Cl.
CPC ............ *A61B 6/5264* (2013.01); *A61B 6/025* (2013.01); *A61B 6/502* (2013.01)

(58) Field of Classification Search
CPC ........ A61B 6/025; A61B 6/502; A61B 6/5264
See application file for complete search history.

(56) References Cited

U.S. PATENT DOCUMENTS

2021/0166443 A1* 6/2021 Morita .................. G06T 11/005

FOREIGN PATENT DOCUMENTS

WO 2020/067475 A1 4/2020

* cited by examiner

*Primary Examiner* — Dani Fox
(74) *Attorney, Agent, or Firm* — SOLARIS Intellectual Property Group, PLLC

(57) ABSTRACT

A CPU of a console acquires a plurality of projection images, performs an optimization process on a forward projection model, which has, as parameters, an absorption coefficient assigned to each voxel of a three-dimensional model that is virtually set in a three-dimensional space in which the object is disposed and has a plurality of voxels as constituent units, an intersection length of each voxel where a path of radiation emitted at an irradiation position intersects the three-dimensional model, and an amount of movement of the object, on the basis of the projection images at each of a plurality of irradiation positions, and generates a tomographic image of the object using the optimized parameters.

14 Claims, 10 Drawing Sheets

BEFORE MOVEMENT

AFTER MOVEMENT

IMAGE PROCESSING DEVICE, RADIOGRAPHY SYSTEM, IMAGE PROCESSING METHOD, AND IMAGE PROCESSING PROGRAM

CROSS-REFERENCE TO RELATED APPLICATIONS

The present application claims priority under 35 U.S.C. § 119 to Japanese Patent Application No. 2021-050391 filed on Mar. 24, 2021. The above application is hereby expressly incorporated by reference, in its entirety, into the present application.

BACKGROUND

1. Technical Field

The present disclosure relates to an image processing device, a radiography system, an image processing method, and an image processing program.

2. Description of the Related Art

In general, so-called tomosynthesis imaging is known which irradiates an object with radiation emitted from a radiation source at each of a plurality of irradiation positions having different irradiation angles to capture a plurality of projection images of the object at different irradiation positions.

In the tomosynthesis imaging, since a plurality of projection images are captured, a positional deviation between the projection images may occur because of the influence of, for example, the movement of the object. There is a problem in that a tomographic image generated using a plurality of projection images having a positional deviation therebetween is a blurred image.

Therefore, a technique which corrects the positional deviation between the projection images, that is, the movement of the object, is known. For example, WO2020/067475A discloses a technique which derives the amount of positional deviation between a plurality of projection images on the basis of a feature point in a tomographic plane corresponding to a tomographic image from which the feature point has been detected and generates a tomographic image using the projection images whose positional deviation has been corrected according to the derived amount of positional deviation.

SUMMARY

However, the projection image is an image onto which a plurality of structures present on an irradiation path of radiation are projected so as to overlap each other and includes a large amount of information. In the above-mentioned technique according to the related art, the movement of the object may not be corrected because of the influence of the information of the structures other than the feature point.

The present disclosure has been made in view of the above circumstances, and an object of the present disclosure is to provide an image processing device, a radiography system, an image processing method, and an image processing program that can correct the movement of an object with high accuracy.

In order to achieve the above object, according to a first aspect of the present disclosure, there is provided an image processing device that processes a plurality of projection images obtained by irradiating an object with radiation emitted from a radiation source at each of a plurality of irradiation positions having different irradiation angles. The image processing device comprises at least one processor. The processor acquires the plurality of projection images, performs an optimization process on a forward projection model, which has, as parameters, an absorption coefficient assigned to each voxel of a three-dimensional model that is virtually set in a three-dimensional space in which the object is disposed and has a plurality of voxels as constituent units, an intersection length of each voxel where a path of the radiation emitted at the irradiation position intersects the three-dimensional model, and an amount of movement of the object, on the basis of the projection images at each of the plurality of irradiation positions, and generates a tomographic image of the object using the optimized parameters.

According to a second aspect of the present disclosure, in the image processing device according to the first aspect, the processor may generate the tomographic image using the absorption coefficient of the optimized forward projection model.

According to a third aspect of the present disclosure, in the image processing device according to the first aspect or the second aspect, as the optimization process, the processor may bring each pixel value of a plurality of pseudo-projection images obtained by performing pseudo-projection at the plurality of irradiation positions using the forward projection model close to each pixel value of the plurality of projection images.

According to a fourth aspect of the present disclosure, in the image processing device according to the third aspect, the processor may perform the optimization process by deriving the absorption coefficient and the amount of movement for bringing the pixel values of the pseudo-projection images close to the pixel values of the plurality of projection images.

According to a fifth aspect of the present disclosure, in the image processing device according to any one of the first to fourth aspects, the processor may derive the amount of movement using the optimized forward projection model.

According to a sixth aspect of the present disclosure, in the image processing device according to any one of the first to fifth aspects, the processor may derive the amount of movement on the basis of a forward projection model using, as the three-dimensional model, a three-dimensional model that is virtually set in a three-dimensional space corresponding to a feature region of the object in the three-dimensional space in which the object is disposed and generate the tomographic image using the derived amount of movement and the forward projection model using the three-dimensional model virtually set in the three-dimensional space in which the object is disposed.

According to a seventh aspect of the present disclosure, in the image processing device according to the sixth aspect, the feature region may be a region including a structure that has a feature amount equal to or greater than a threshold value.

According to an eighth aspect of the present disclosure, in the image processing device according to the seventh aspect, the object may be a breast, and the structure may be at least one of a calcification or a mammary gland.

According to a ninth aspect of the present disclosure, in the image processing device according to any one of the first to eighth aspects, the processor may perform the optimization process on a first forward projection model using a voxel with a first size and may perform the optimization process on a second forward projection model using a voxel with a second size smaller than the first size, using the absorption coefficient and the amount of movement of the optimized first forward projection model as initial values.

According to a tenth aspect of the present disclosure, in the image processing device according to the ninth aspect, the processor may repeat the optimization process while reducing the size of the voxel used.

According to an eleventh aspect of the present disclosure, in the image processing device according to any one of the first to tenth aspects, the processor may estimate the forward projection model using an energy function defined by the absorption coefficient, the intersection length, and the amount of movement.

In addition, in order to achieve the above object, according to a twelfth aspect of the present disclosure, there is provided a radiography system comprising: a radiation source that generates radiation; a radiography apparatus that performs tomosynthesis imaging which irradiates an object with the radiation emitted from the radiation source at each of a plurality of irradiation positions having different irradiation angles to capture projection images of the object at each of the irradiation positions; and the image processing device according to the present disclosure.

Further, in order to achieve the above object, according to a thirteenth aspect of the present disclosure, there is provided an image processing method that is executed by a computer and that processes a plurality of projection images obtained by irradiating an object with radiation emitted from a radiation source at each of a plurality of irradiation positions having different irradiation angles. The image processing method comprises: acquiring the plurality of projection images; performing an optimization process on a forward projection model, which has, as parameters, an absorption coefficient assigned to each voxel of a three-dimensional model that is virtually set in a three-dimensional space in which the object is disposed and has a plurality of voxels as constituent units, an intersection length of each voxel where a path of the radiation emitted at the irradiation position intersects the three-dimensional model, and an amount of movement of the object, on the basis of the projection images at each of the plurality of irradiation positions; and generating a tomographic image of the object using the optimized parameters.

Furthermore, in order to achieve the above object, according to a fourteenth aspect of the present disclosure, there is provided an image processing program that processes a plurality of projection images obtained by irradiating an object with radiation emitted from a radiation source at each of a plurality of irradiation positions having different irradiation angles. The image processing program causes a computer to perform a process comprising: acquiring the plurality of projection images; performing an optimization process on a forward projection model, which has, as parameters, an absorption coefficient assigned to each voxel of a three-dimensional model that is virtually set in a three-dimensional space in which the object is disposed and has a plurality of voxels as constituent units, an intersection length of each voxel where a path of the radiation emitted at the irradiation position intersects the three-dimensional model, and an amount of movement of the object, on the basis of the projection images at each of the plurality of irradiation positions; and generating a tomographic image of the object using the optimized parameters.

According to the present disclosure, it is possible to correct the movement of the object with high accuracy.

BRIEF DESCRIPTION OF THE DRAWINGS

Exemplary embodiments according to the technique of the present disclosure will be described in detail based on the following figures, wherein.

DETAILED DESCRIPTION

Hereinafter, an embodiment of the present disclosure will be described in detail with reference to the drawings. In addition, this embodiment does not limit the present disclosure.

Figure 1:
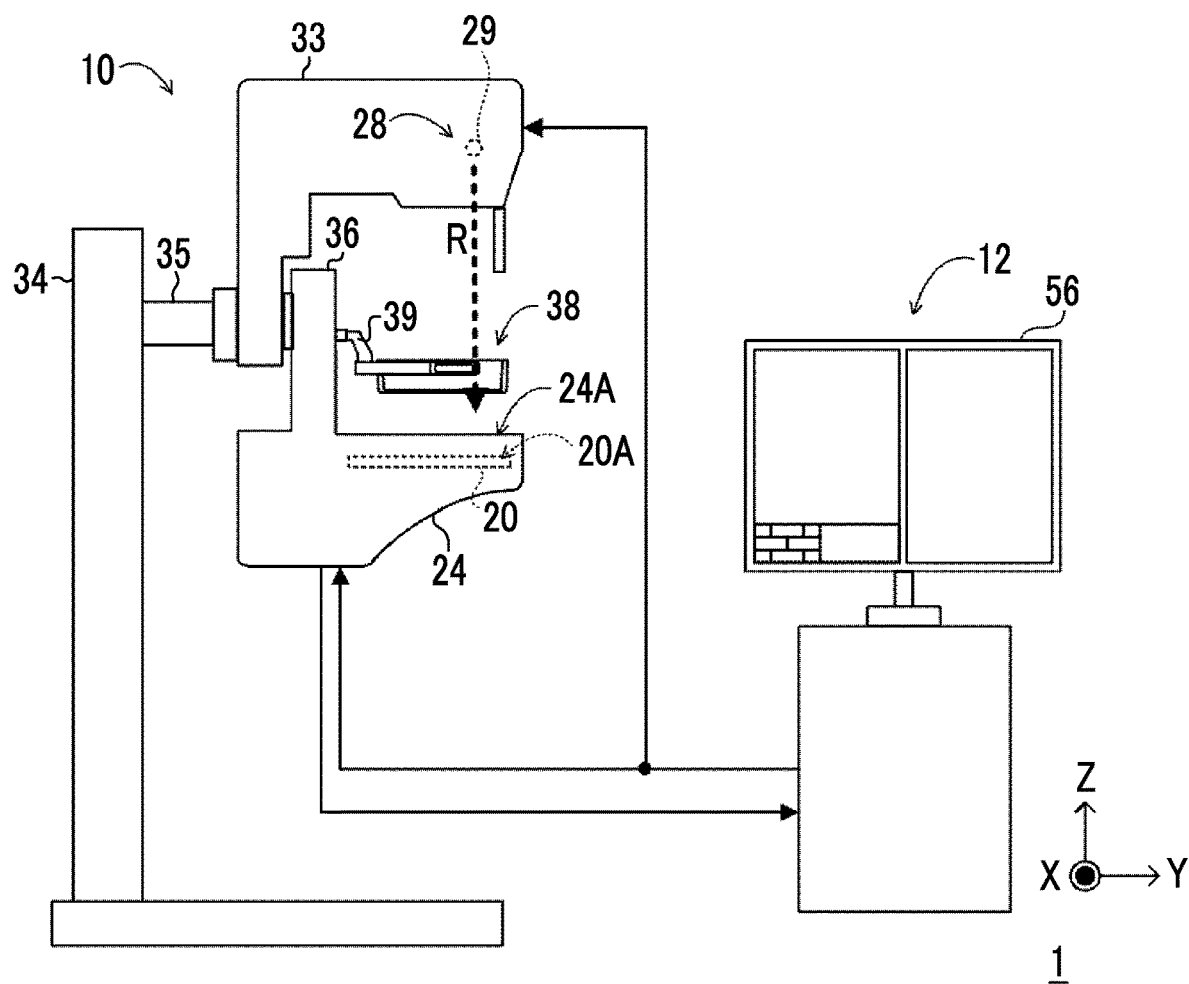
FIG. 1 is a diagram schematically illustrating an example of the overall configuration of a radiography system according to an embodiment.

First, an example of the overall configuration of a radiography system according to this embodiment will be described. FIG. 1 is a diagram illustrating an example of the overall configuration of a radiography system 1 according to this embodiment. As illustrated in FIG. 1, the radiography system 1 according to this embodiment comprises a mammography apparatus 10 and a console 12.

First, the mammography apparatus 10 according to this embodiment will be described. FIG. 1 is a side view illustrating an example of the outward appearance of the mammography apparatus 10 according to this embodiment. In addition, FIG. 1 illustrates an example of the outward appearance of the mammography apparatus 10 as viewed from a left side of a subject.

The mammography apparatus 10 according to this embodiment is an apparatus that is operated under the control of the console 12 and that irradiates a breast of the subject as an object with radiation R (for example, X-rays) to capture a radiographic image of the breast. In addition, the mammography apparatus 10 may be an apparatus that images the breast of the subject not only in a state in which the subject is standing (standing state) but also in a state in which the subject is sitting on, for example, a chair (including a wheelchair) (sitting state).

Furthermore, the mammography apparatus 10 according to this embodiment has a function of performing normal imaging that captures images at an irradiation position where a radiation source 29 is disposed along a normal direction to a detection surface 20A of a radiation detector 20 and so-called tomosynthesis imaging that captures images while moving the radiation source 29 to each of a plurality of irradiation positions.

The radiation detector 20 detects the radiation R transmitted through the breast which is the object. Specifically, the radiation detector 20 detects the radiation R that has entered the breast of the subject and an imaging table 24 and that has reached the detection surface 20A of the radiation detector 20, generates a radiographic image on the basis of the detected radiation R, and outputs image data indicating the generated radiographic image. In the following description, in some cases, a series of operations of emitting the radiation R from the radiation source 29 and generating a radiographic image using the radiation detector 20 is referred to as "imaging". On the detection surface 20A of the radiation detector 20 according to this embodiment, i pixels (see pixels $21_i$ (i=1, 2, . . . ,) in FIG. 5) corresponding to the radiographic image generated by the radiation detector 20 are arranged in a matrix. The type of the radiation detector 20 according to this embodiment is not particularly limited. For example, the radiation detector 20 may be an indirect-conversion-type radiation detector that converts the radiation R into light and converts the converted light into charge or a direct-conversion-type radiation detector that directly converts the radiation R into charge.

As illustrated in FIG. 1, the radiation detector 20 is disposed in the imaging table 24. In the mammography apparatus 10 according to this embodiment, in a case in which imaging is performed, the breast of the subject is positioned on an imaging surface 24A of the imaging table 24 by a user.

A compression plate 38 that is used to compress the breast in a case in which imaging is performed is attached to a compression unit 36 that is provided in the imaging table 24. Specifically, the compression unit 36 is provided with a compression plate driving unit (not illustrated) that moves the compression plate 38 in a direction (hereinafter, referred to as an "up-down direction") toward or away from the imaging table 24. A support portion 39 of the compression plate 38 is detachably attached to the compression plate driving unit and is moved in the up-down direction by the compression plate driving unit to compress the breast of the subject between the compression plate 38 and the imaging table 24. The compression plate 38 according to this embodiment is an example of a compression member according to the present disclosure.

As illustrated in FIG. 1, the mammography apparatus 10 according to this embodiment comprises the imaging table 24, an arm portion 33, a base 34, and a shaft portion 35. The arm portion 33 is held by the base 34 so as to be movable in the up-down direction (Z-axis direction). In addition, the arm portion 33 can be rotated with respect to the base 34 by the shaft portion 35. The shaft portion 35 is fixed to the base 34, and the shaft portion 35 and the arm portion 33 are rotated integrally.

Gears are provided in each of the shaft portion 35 and the compression unit 36 of the imaging table 24. The gears can be switched between an engaged state and a non-engaged state to switch between a state in which the compression unit 36 of the imaging table 24 and the shaft portion 35 are connected and rotated integrally and a state in which the shaft portion 35 is separated from the imaging table 24 and runs idle. In addition, components for switching between transmission and non-transmission of power of the shaft portion 35 are not limited to the gears, and various mechanical elements may be used.

Each of the arm portion 33 and the imaging table 24 can be relatively rotated with respect to the base 34, using the shaft portion 35 as a rotation axis. In this embodiment, engagement portions (not illustrated) are provided in each of the base 34, the arm portion 33, and the compression unit 36 of the imaging table 24. The state of the engagement portions is switched to connect each of the arm portion 33 and the compression unit 36 of the imaging table 24 to the base 34. One or both of the arm portion 33 and the imaging table 24 connected to the shaft portion 35 are integrally rotated on the shaft portion 35.

Figure 2:
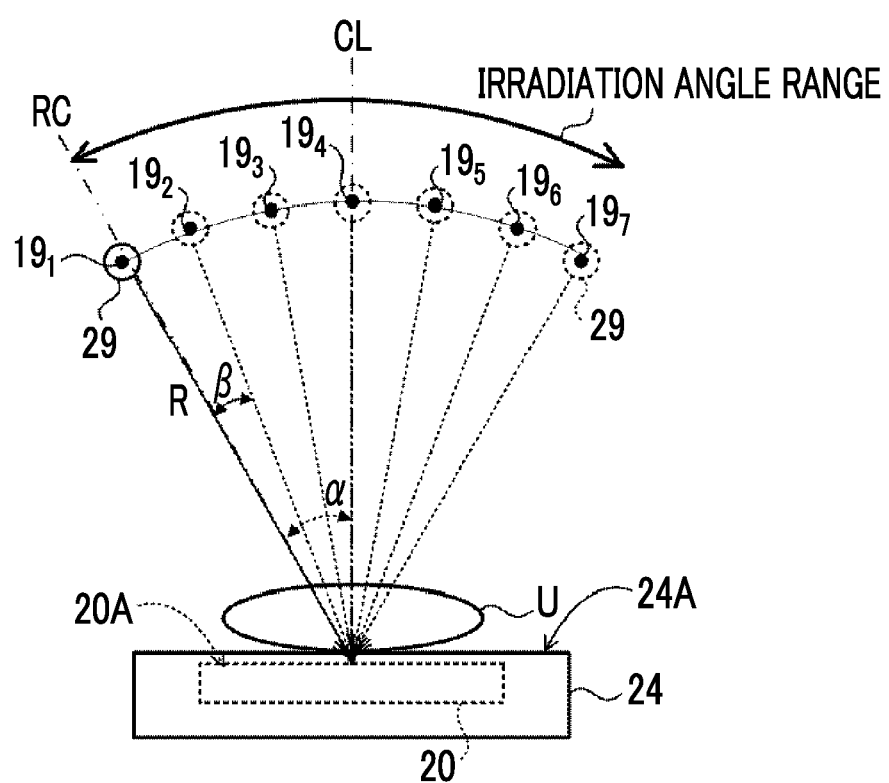
FIG. 2 is a diagram illustrating an example of tomosynthesis imaging.

In a case in which the mammography apparatus 10 performs the tomosynthesis imaging, the radiation source 29 of a radiation emitting unit 28 is sequentially moved to each of the plurality of irradiation positions having different irradiation angles by the rotation of the arm portion 33. The radiation source 29 includes a radiation tube (not illustrated) that generates the radiation R, and the radiation tube is moved to each of the plurality of irradiation positions according to the movement of the radiation source 29. FIG. 2 is a diagram illustrating an example of the tomosynthesis imaging. In addition, the compression plate 38 is not illustrated in FIG. 2. In this embodiment, as illustrated in FIG. 2, the radiation source 29 is moved to irradiation positions $19_t$ (t=1, 2, . . . ; the maximum value is 7 in FIG. 2) having different irradiation angles which are arranged at an interval of a predetermined angle θ, that is, positions where the radiation R is emitted to the detection surface 20A of the radiation detector 20 at different angles. At each of the irradiation positions $19_t$, the radiation source 29 emits the radiation R to a breast W in response to an instruction from the console 12, and the radiation detector 20 captures a radiographic image. In the radiography system 1, in a case in which the tomosynthesis imaging that moves the radiation source 29 to each of the irradiation positions $19_t$ and that captures radiographic images at each of the irradiation positions $19_t$ is performed, seven radiographic images are obtained in the example illustrated in FIG. 2. In addition, in the following description, in the tomosynthesis imaging, in a case in which a radiographic image captured at each irradiation position 19 is distinguished from other radiographic images, it is referred to as a "projection image". Further, in a case in which a radiographic image is generically referred to regardless of the type, such as a projection image and a tomographic image which will be described below, it is simply referred to as a "radiographic image". Furthermore, in the following description, in a case in which the irradiation positions $19_t$ are generically referred to, a reference letter t for distinguishing each irradiation position is omitted, and the irradiation positions $19_t$ are referred to as "irradiation positions 19". Further, in the following description, for the image corresponding to the irradiation position $19_t$, such as the projection image captured at each irradiation position $19_t$, the reference letter t indicating the irradiation position $19_t$ is given to the reference numeral indicating each image.

In addition, as illustrated in FIG. 2, the irradiation angle of the radiation R means an angle α formed between a normal line CL to the detection surface 20A of the radiation detector 20 and a radiation axis RC. The radiation axis RC means an axis that connects the focus of the radiation source 29 at each irradiation position 19 and a preset position such as the center of the detection surface 20A. Further, here, it is assumed that the detection surface 20A of the radiation detector 20 is substantially parallel to the imaging surface 24A.

On the other hand, in a case in which the mammography apparatus 10 performs the normal imaging, the radiation source 29 of the radiation emitting unit 28 remains at the irradiation position $19_t$ (the irradiation position $19_t$ along the normal direction, the irradiation position $19_4$ in FIG. 2) where the irradiation angle α is 0 degrees. The radiation source 29 emits the radiation R in response to an instruction from the console 12, and the radiation detector 20 captures a radiographic image.

Figure 3:
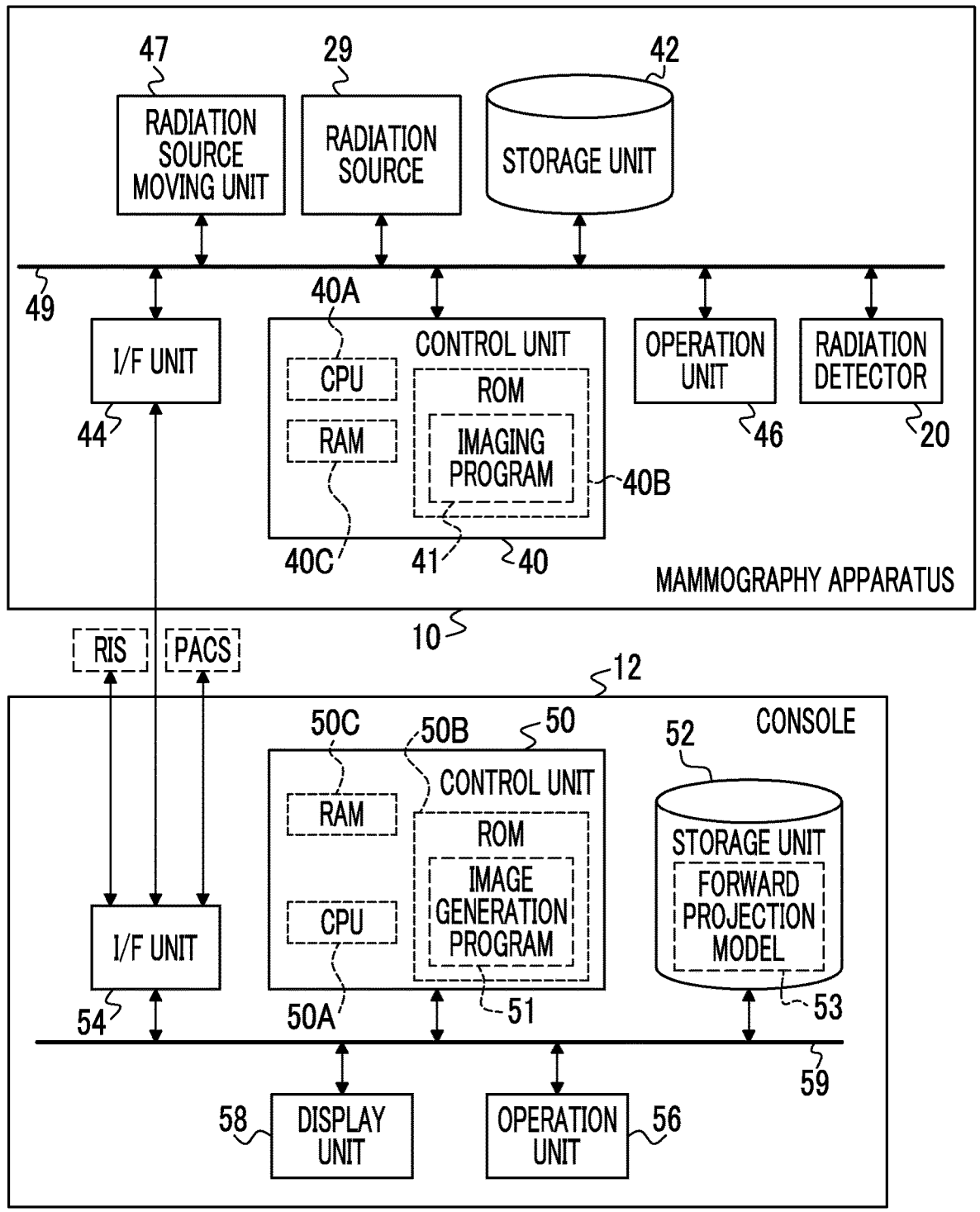
FIG. 3 is a block diagram illustrating an example of the configuration of a mammography apparatus and a console according to the embodiment.

Further, FIG. 3 is a block diagram illustrating an example of the configuration of the mammography apparatus 10 and the console 12 according to this embodiment. As illustrated in FIG. 3, the mammography apparatus 10 according to this embodiment further comprises a control unit 40, a storage unit 42, an interface (I/F) unit 44, an operation unit 46, and a radiation source moving unit 47. The control unit 40, the storage unit 42, the I/F unit 44, the operation unit 46, and the radiation source moving unit 47 are connected to each other through a bus 49, such as a system bus or a control bus, such that they can transmit and receive various kinds of information.

The control unit 40 controls the overall operation of the mammography apparatus 10 under the control of the console 12. The control unit 40 comprises a central processing unit (CPU) 40A, a read only memory (ROM) 40B, and a random access memory (RAM) 40C. For example, various programs including an imaging program 41 which is executed by the CPU 40A and which performs control related to the capture of a radiographic image are stored in the ROM 40B in advance. The RAM 40C temporarily stores various kinds of data.

For example, the image data of the radiographic image captured by the radiation detector 20 and various other kinds of information are stored in the storage unit 42. A specific example of the storage unit 42 is a hard disk drive (HDD), a solid state drive (SSD), or the like. The I/F unit 44 transmits and receives various kinds of information to and from the console 12 using wireless communication or wired communication. The image data of the radiographic image captured by the radiation detector 20 in the mammography apparatus 10 is transmitted to the console 12 through the I/F unit 44 by wireless communication or wired communication.

Each of the control unit 40, the storage unit 42, and the I/F unit 44 according to this embodiment is provided in the imaging table 24.

In addition, the operation unit 46 is provided as a plurality of switches in, for example, the imaging table 24 of the mammography apparatus 10. Further, the operation unit 46 may be provided as a touch panel switch or may be provided as a foot switch that is operated by the feet of the user such as a doctor or a radiology technician.

The radiation source moving unit 47 has a function of moving the radiation source 29 to each of the plurality of irradiation positions 19 under the control of the control unit 40 in a case in which the tomosynthesis imaging is performed as described above. Specifically, the radiation source moving unit 47 rotates the arm portion 33 with respect to the imaging table 24 to move the radiation source 29 to each of the plurality of irradiation positions 19. The radiation source moving unit 47 according to this embodiment is provided inside the arm portion 33.

On the other hand, the console 12 according to this embodiment has a function of controlling the mammography apparatus 10 using, for example, an imaging order and various kinds of information acquired from a radiology information system (RIS) through a wireless communication local area network (LAN) and instructions input by the user through an operation unit 56 or the like.

For example, the console 12 according to this embodiment is a server computer. As illustrated in FIG. 3, the console 12 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C. Various programs which are executed by the CPU 50A and which include an image generation program 51 are stored in the ROM 50B in advance. The RAM 50C temporarily stores various kinds of data. In this embodiment, the CPU 50A is an example of a processor according to the present disclosure, and the console 12 is an example of an image processing device according to the present disclosure. In addition, the image generation program 51 according to this embodiment is an example of an image processing program according to the present disclosure.

For example, the image data of the radiographic image captured by the mammography apparatus 10 and various other kinds of information are stored in the storage unit 52. Further, the storage unit 52 stores a forward projection model 53 which will be described in detail below. A specific example of the storage unit 52 is an HDD, an SSD, or the like.

The operation unit 56 is used by the user to input, for example, instructions which are related to the capture of a radiographic image and which include an instruction to emit the radiation R or various kinds of information. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information to and from the mammography apparatus 10, the RIS, and a picture archiving and communication system (PACS) using wireless communication or wired communication. In the radiography system 1 according to this embodiment, the console 12 receives the image data of the radiographic image captured by the mammography apparatus 10 from the mammography apparatus 10 through the I/F unit 54, using wireless communication or wired communication.

Figure 4:
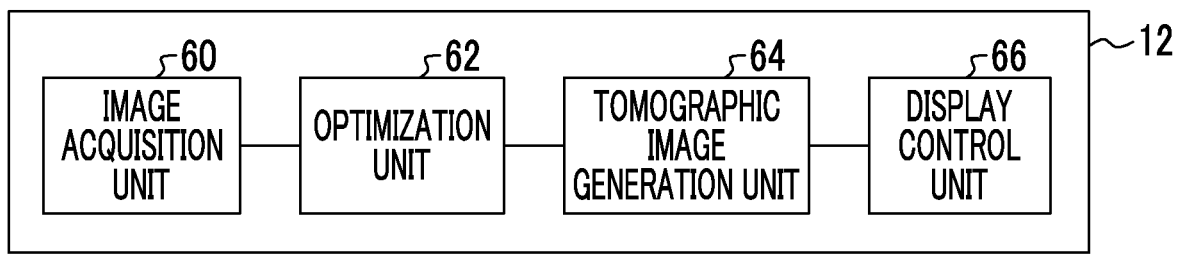
FIG. 4 is a functional block diagram illustrating an example of the functions of the console according to the embodiment.

The console 12 according to this embodiment has a function of correcting the movement of the object in the tomosynthesis imaging. FIG. 4 is a functional block diagram illustrating an example of a configuration related to the function of correcting the movement of the object in the tomosynthesis imaging in the console 12 according to this embodiment. As illustrated in FIG. 4, the console 12 comprises an image acquisition unit 60, an optimization unit 62, a tomographic image generation unit 64, and a display control unit 66. For example, in the console 12 according to this embodiment, the CPU 50A of the control unit 50 executes the image generation program 51 stored in the ROM 50B to function as the image acquisition unit 60, the optimization unit 62, the tomographic image generation unit 64, and the display control unit 66.

The image acquisition unit 60 has a function of acquiring a plurality of projection images. Specifically, the image acquisition unit 60 according to this embodiment acquires image data indicating a plurality of projection images obtained by the tomosynthesis imaging in the mammography apparatus 10. The image acquisition unit 60 outputs the acquired image data indicating the plurality of projection images to the optimization unit 62.

The optimization unit 62 has a function of performing an optimization process on the forward projection model 53 on the basis of the projection images at each of the plurality of irradiation positions 19.

The forward projection model 53 is a model for performing forward projection that projects data from a three-dimensional space, which is a real space, onto the detection surface 20A of the radiation detector 20. The forward projection model 53 will be described with reference to FIG. 5.

Figure 5:
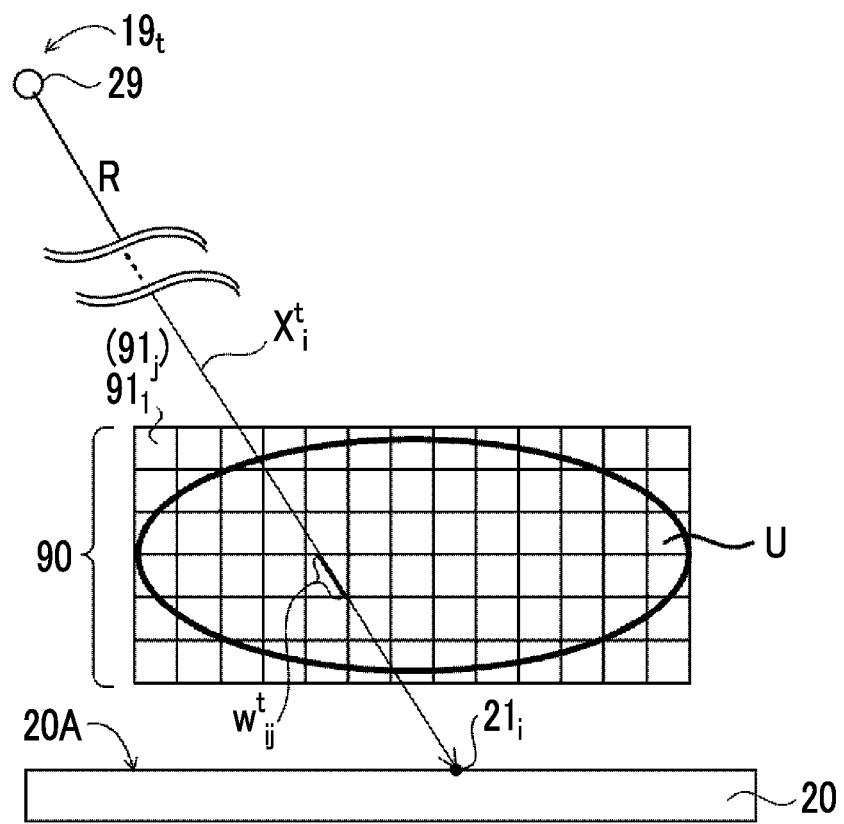
FIG. 5 is a diagram illustrating a forward projection model.

As illustrated in FIG. 5, a three-dimensional model 90 having a plurality of voxels $91_j$ (j=1, 2, ..., J) as constituent units is virtually set in the three-dimensional space in which an object U is disposed. For example, the space in which the optimization unit 62 according to this embodiment sets the three-dimensional model 90 is a space in which the object U is presumed to be present according to the imaging table 24 or the like.

FIG. 5 illustrates a path $X^t_i$ of the radiation R emitted from the radiation source 29 that is located at the irradiation position $19_t$ to a pixel $21_i$ of the radiation detector 20. It is assumed that the intersection length of each voxel $91_j$ where the path $X^t_i$ intersects each voxel $91_j$ of the three-dimensional model 90 is $w^t_{ij}$ and an absorption coefficient of each voxel $91_j$ is represented as follows.

$$\mu^t = (\mu_1, \mu_2, \ldots, \mu_j)^T$$

In a case in which the radiation R is emitted at the irradiation position $19_t$, the forward projection model 53 indicating the number of photons $p^t_i$ detected by an i-th pixel of the radiation detector 20 is represented by the following Expression (1).

$$p^t_i = b^t_i \exp\left(-\sum_j w^t_{ij} \mu_j\right) \quad (1)$$

Here, the logarithm of the above-described Expression (1) is taken, the logarithm of the number of photons $p^t_i$ measured by the radiation detector 20 is $y^t_i$, and each variable is described in a vector format as follows:

$$y^t = (y_1^t, y_2^t, \ldots, y_I^t)^T$$

From here, the intersection length $w^t_{ij}$ with the voxel $91_j$ is described by a determinant as in the following Expression (2).

$$W^t = \begin{bmatrix} w^t_{11} & \cdots & w^t_{1J} \\ \vdots & \ddots & \vdots \\ w^t_{I1} & \cdots & w^t_{IJ} \end{bmatrix} \quad (2)$$

The projection process can be represented by a determinant represented by the following Expression (3).

$$y^t = W^t \mu \quad (3)$$

The above-described Expression (3) is formulated for each of T projection images obtained at each irradiation position $19_t$. In this case, the absorption coefficient μ can be derived by solving simultaneous equations represented by the following Expression (4).

$$\begin{cases} y^1 = W^1 \mu \\ \vdots \\ y^T = W^T \mu \end{cases} \quad (4)$$

However, since the size of the determinant indicating the intersection length $w^t_{ij}$ represented by the above-described Expression (2) is large, it is not easy to solve the simultaneous equations represented by the above-described Expression (4). In addition, since the number of projection images T obtained by the tomosynthesis imaging is generally relatively small, there is an ill-posed problem that the number of equations is insufficient for the above-described Expression (4). Therefore, for example, in this embodiment, the parameter μ satisfying the above-described Expression (1) indicating the forward projection model 53 is optimized, and the following Expression (5) is minimized for the optimization. As a specific method, the following Expression (5) may be minimized by a gradient method or the like. In addition, the following Expression (5) is introduced as an example of the estimation of μ. However, other expressions, such as the addition of a condition for μ, can be sufficiently considered. An energy function may be minimized, and it goes without saying that the present disclosure is not limited to this expression. Further, "optimizing" and "minimizing" mean "performing an optimization process" and "performing a minimization process", respectively, and may be any other methods that can find a better solution.

$$\mu = \underset{\mu}{\operatorname{argmin}} \sum_t (y^t - W^t \mu)^2 \quad (5)$$

Figure 6:
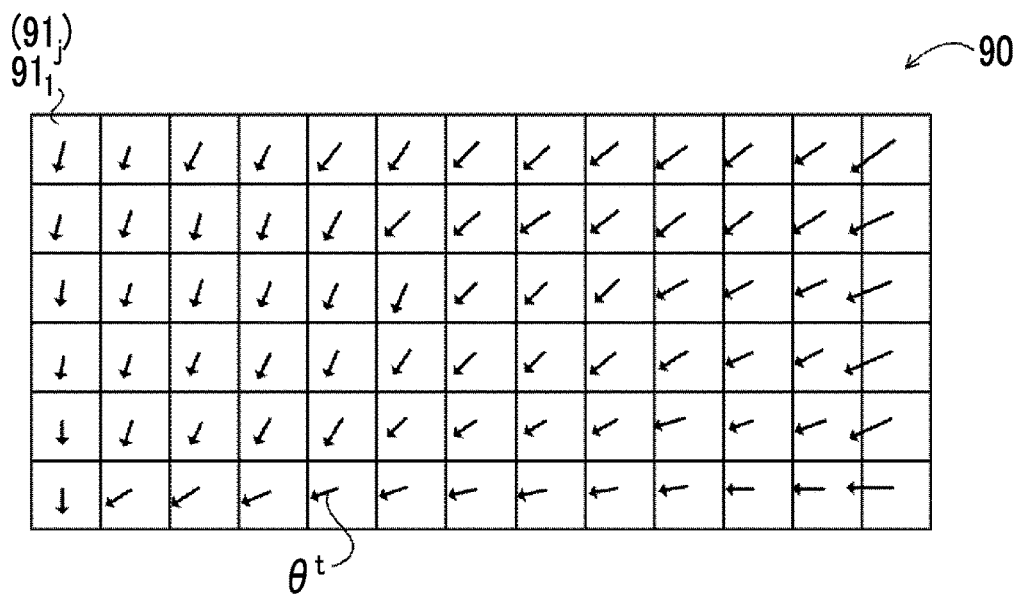
FIG. 6 is a diagram illustrating an amount of movement for each voxel.
Figure 7:
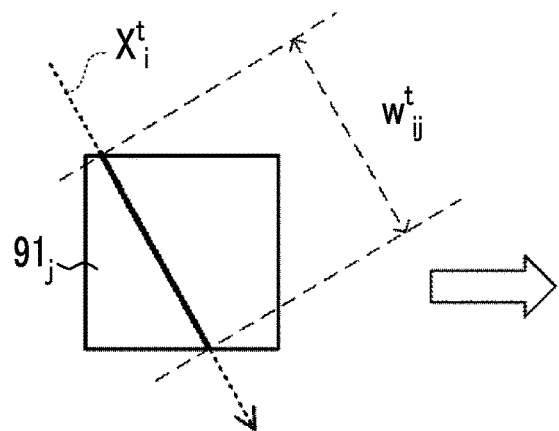
FIG. 7 is a diagram illustrating a relationship between the amount of movement and an intersection length for each voxel.
Figure 7:
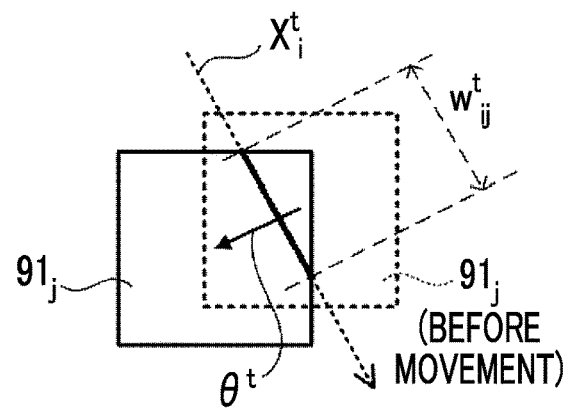

The intersection length $w^t_{ij}$ of each voxel $91_j$ where the path $X^t_i$ intersects each voxel $91_j$ of the three-dimensional model 90 changes depending on the movement of the object U. As illustrated in FIG. 6, the amount of movement of the object U is defined as a vector $\theta^t$. The amount of movement $\theta^t$ can be defined as, for example, a vector from the center of gravity of the voxel $91_j$ before the position changes to the center of gravity of the voxel $91_j$ after the position changes. In addition, assuming that a different amount of movement $\theta^t$ is generated for each pixel $21i$, the amount of movement $\theta^t$ is used as a variable for each pixel $21_i$ and may be defined as $\theta^t = (\theta^t_1, \theta^t_2, \ldots, \theta^t_I)$. FIG. 7 illustrates a change in the intersection length $w^t_{ij}$ caused by the movement of the object U. Since the three-dimensional model 90 corresponds to the three-dimensional space in which the object U is disposed, the position of the three-dimensional model 90 changes in operative association with the movement of the object U. In other words, the position of the voxel $91_j$ of the three-dimensional model 90 varies depending on the movement of the object U. As illustrated in FIG. 7, even in a case in which the position of the voxel $91_j$ changes, the path $X^t_i$ of the radiation R does not change. Therefore, the intersection length $w^t_{ij}$ of the path $X^t_i$ intersecting the voxel $91_j$ changes depending on the movement of the object U.

In a case in which the movement of the object U occurs, the forward projection model 53 can be expressed using an energy function of the following Expression (6). In addition, two variables of the absorption coefficient μ and the amount of movement $θ_t$ need to be optimized at the same time in order to solve the following Expression (6). The optimization of the absorption coefficient μ and the optimization of the amount of movement $θ^t$ can be sequentially repeated to derive the solution.

$$\mu, \theta = \operatorname*{argmin}_{\mu,\theta} \sum_t (y^t - W(\theta^t)\mu)^2 \quad (6)$$

The forward projection model 53 in a case in which the movement of the object U occurs as described above is defined by the absorption coefficient μ assigned to each voxel $91_j$ of the three-dimensional model 90, the intersection length $w^t_{ij}$ of each voxel $91_j$, and the amount of movement $θ^t$ of the object U. In addition, a method for deriving the intersection length $w^t_{ij}$ is not particularly limited. A geometric method may be applied, or the intersection length $w^t_{ij}$ may be derived by approximate calculation.

Pseudo-projection is performed at the irradiation position $19_t$ using the forward projection model 53 in a case in which the movement of the object U occurs to obtain a pseudo-projection image in a case in which the movement of the object U occurs. A process of optimizing the forward projection model 53 means a process of bringing the pseudo-projection image obtained using the forward projection model 53 close to the projection image actually obtained by the tomosynthesis imaging to bring the forward projection model 53 close to the disposition state of the object U including the movement in a case in which the tomosynthesis imaging is actually performed. The absorption coefficient μ and the amount of movement $θ^t$ of the optimized forward projection model 53 correspond to the disposition state and movement of the object U in a case in which the projection image is actually captured by the tomosynthesis imaging.

The optimization unit 62 has a function of performing the optimization process on the forward projection model 53 as described above. Specifically, the optimization unit 62 virtually sets the three-dimensional model 90 having a plurality of voxels $91_j$ as constituent units in the three-dimensional space in which the object U is disposed. In addition, the optimization unit 62 acquires a plurality of projection images actually captured by the tomosynthesis imaging and a plurality of irradiation positions $19_t$ where the projection images have been captured. The optimization unit 62 solves the energy function of the above-described Expression (6) using the acquired information to perform the optimization process on the forward projection model 53. The optimization unit 62 outputs the absorption coefficient μ and the amount of movement $θ^t$ obtained by the optimized forward projection model 53 to the tomographic image generation unit 64. In addition, in a case in which the energy function of the above-described Expression (6) is solved, a process of bringing the pixel value of each pixel of the pseudo-projection image obtained by performing pseudo-projection using the forward projection model 53 close to the pixel value of each pixel of the corresponding projection image is performed. Therefore, T images which are a plurality of pseudo-projection images are not obtained.

Figure 8:
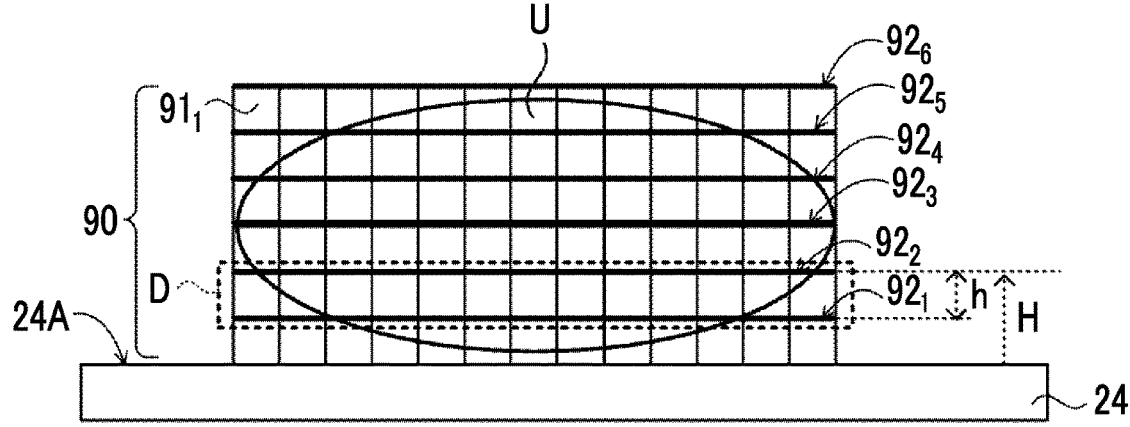
FIG. 8 is a diagram illustrating a method for generating a tomographic image.

The tomographic image generation unit 64 has a function of generating a tomographic image of the breast which is the object U. Specifically, a plurality of tomographic images in each of a plurality of tomographic planes of the object U are generated. An example of a tomographic image generation method in the tomographic image generation unit 64 according to this embodiment will be described with reference to FIG. 8. In the example illustrated in FIG. 8, an aspect in which a tomographic image corresponding to the size of the voxel $91_j$ is illustrated. Tomographic planes $92_1$ to $92_6$ in which the tomographic images are generated are substantially parallel to the imaging surface 24A of the imaging table 24, and a slice thickness of the tomographic image which is an interval h between the tomographic planes 92 is determined by the size of the irradiation position $19_t$. In addition, a height H of the tomographic image means a height from the imaging surface 24A of the imaging table 24 to the tomographic plane corresponding to the tomographic image. FIG. 8 illustrates the height H to the tomographic plane $92_2$.

In a case in which the tomographic image generation unit 64 generates a tomographic image in the tomographic plane $92_2$, it generates the tomographic image using the absorption coefficient μ of each of the plurality of voxels $91_j$ whose upper surfaces come into contact with the tomographic plane $92_2$. In the example illustrated in FIG. 8, the tomographic image generation unit 64 generates a tomographic image using the absorption coefficient μ of each of the voxels $91_j$ in a region surrounded by a dotted line D.

In addition, the radiographic image obtained by the normal imaging is displayed as a radiographic image using, for example, a value obtained by performing logarithmic conversion on the number of photons detected by the radiation detector 20 or a value obtained by performing look-up table (LUT) conversion on the number of photons. Therefore, similarly, the absorption coefficients μ may be displayed as a tomographic image using a value obtained by, for example, logarithmic conversion or LUT conversion. As described above, the display form of the tomographic image generated using the forward projection model 53 is the same as the display form of the normal imaging such that the image appears in the same form, which makes it possible for the user to easily interpret the image.

Further, in this embodiment, the interval h between the tomographic planes 92 of the tomographic images generated by the tomographic image generation unit 64 is the same as the size of the voxel $91_j$. However, the interval h between the tomographic planes 92 is not limited to this aspect. For example, the interval h may be specified by the user. In this case, the tomographic image generation unit 64 may generate a tomographic image using the absorption coefficients μ of the voxels $91_j$ corresponding to the tomographic plane 92 which corresponds to the designated interval h or the absorption coefficients μ of the surrounding voxels $91_j$.

The tomographic image generation unit 64 outputs image data indicating the generated plurality of tomographic images to the display control unit 66.

The display control unit 66 has a function of displaying the plurality of tomographic images generated by the tomographic image generation unit 64 on the display unit 58. In addition, the display destination of the tomographic images is not limited to the display unit 58. For example, the display destination may be an image reading device or the like outside the radiography system 1.

Next, the operation of the console 12 in the tomosynthesis imaging will be described with reference to the drawings. After the mammography apparatus 10 performs the tomosynthesis imaging, the console 12 generates a tomographic image using a plurality of projection images obtained by the tomosynthesis imaging and displays the tomographic image on, for example, the display unit 58.

For example, in a case in which the tomosynthesis imaging ends, the mammography apparatus 10 according to this embodiment outputs image data of the captured plurality of projection images 80 to the console 12. The console 12 stores the image data of the plurality of projection images 80 input from the mammography apparatus 10 in the storage unit 52.

Figure 9:
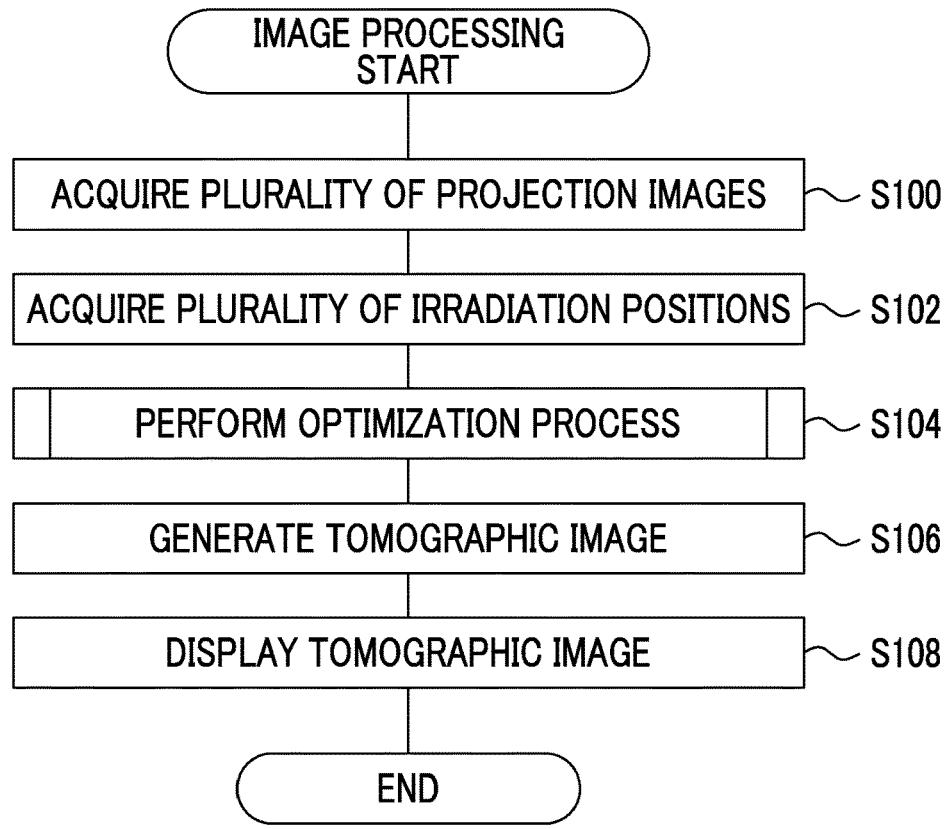
FIG. 9 is a flowchart illustrating an example of the flow of image processing by the console according to the embodiment.

After storing the image data of the plurality of projection images 80 in the storage unit 52, the console 12 performs image processing illustrated in FIG. 9. FIG. 9 is a flowchart illustrating an example of the flow of the image processing performed by the console 12 according to this embodiment. In the console 12 according to this embodiment, for example, the CPU 50A of the control unit 50 executes the image generation program 51 stored in the ROM 50B to perform the image processing whose example is illustrated in FIG. 9.

In Step S100 of FIG. 9, the image acquisition unit 60 acquires a plurality of projection images. As described above, the image acquisition unit 60 according to this embodiment acquires image data of the plurality of projection images from the storage unit 52.

Then, in Step S102, the optimization unit 62 acquires a plurality of irradiation positions $19_t$ which are the irradiation positions 19 of the radiation source 29 where the projection images acquired in Step S100 have been captured. In this step, the optimization unit 62 acquires information indicating the irradiation positions $19_t$ corresponding to each projection image in order to perform the optimization process on the forward projection model 53 for each pixel on the basis of the projection images at each of the plurality of irradiation positions $19_t$. In addition, a method by which the optimization unit 62 acquires the irradiation positions $19_t$ corresponding to the projection images is not particularly limited. For example, the optimization unit 62 may acquire the information indicating the irradiation positions $19_t$ from the mammography apparatus 10. Further, for example, in a case in which the information indicating the irradiation positions $19_t$ is given as imaging information to the projection images, the information indicating the irradiation positions $19_t$ may be acquired from the imaging information given to the acquired projection images.

Then, in Step S104, the optimization unit 62 performs the optimization process, which will be described in detail below, on the forward projection model 53 as described above. The optimization unit 62 performs the optimization process on the forward projection model 53 to derive the absorption coefficient µ and the amount of movement $θ^t$.

Then, in Step S106, the tomographic image generation unit 64 generates the tomographic image of the breast which is the object U. As described above, the tomographic image generation unit 64 generates a plurality of tomographic images using the absorption coefficient µ obtained by the forward projection model 53 optimized in Step S104.

Then, in Step S108, the display control unit 66 displays the tomographic images generated in Step S106 on the display unit 58. In a case in which the process in Step S108 ends, the image processing illustrated in FIG. 9 ends. Further, in this embodiment, the aspect in which the tomographic image is generated in Step S106 and the generated tomographic image is displayed in Step S108 has been described. However, the radiographic image to be generated is not limited to the tomographic image, and the radiographic image to be displayed is not limited to the tomographic image.

For example, the tomographic image generation unit 64 may further generate a composite two-dimensional image obtained by combining at least some of the generated plurality of tomographic images. In addition, a method by which the tomographic image generation unit 64 generates the composite two-dimensional image is not particularly limited. A known method, such as the method described in U.S. Pat. No. 8,983,156B or the method described in JP2014-128716A, can be used.

Figure 10:
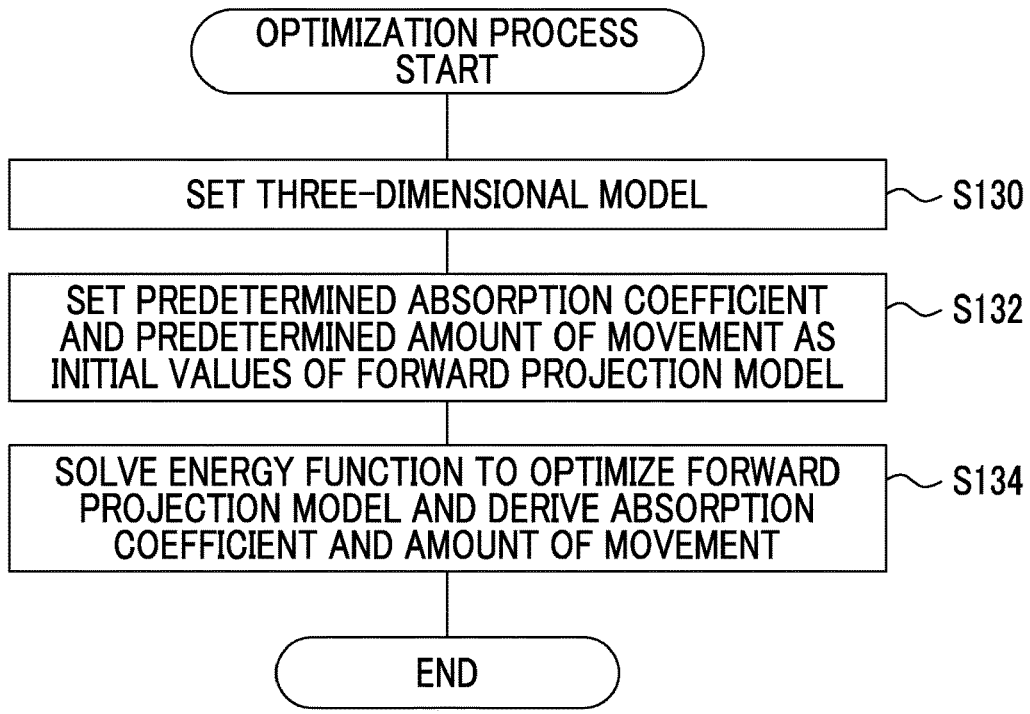
FIG. 10 is a flowchart illustrating an example of the flow of an optimization process in the image processing.

Further, the details of the optimization process in Step S104 of the image processing will be described. FIG. 10 is a flowchart illustrating an example of the flow of the optimization process.

In Step S130 of FIG. 10, the optimization unit 62 sets the three-dimensional model 90 in a three-dimensional space. As described above with reference to FIG. 5, the optimization unit 62 sets the three-dimensional model 90 having the voxel $91_j$ with a predetermined size as a constituent unit in the three-dimensional space in which the object U is presumed to be present in advance according to the imaging table 24. The predetermined size of the voxel $91_j$ is not particularly limited and may be determined in consideration of, for example, the size of the object U or a processing load applied to the optimization process on the forward projection model 53.

Then, in Step S132, the optimization unit 62 sets a predetermined absorption coefficient µ and a predetermined amount of movement $θ^t$ as the initial values of the forward projection model 53 and then proceeds to Step S134. In addition, the predetermined absorption coefficient µ and the predetermined amount of movement $θ^t$ are not particularly limited. For example, an average absorption coefficient µ and an average amount of movement $θ^t$ obtained by experiments may be applied as the predetermined absorption coefficient µ and the predetermined amount of movement $θ^t$, respectively.

Then, in Step S134, the optimization unit 62 solves the energy function of the forward projection model 53 to perform the optimization process on the forward projection model 53 and derives the absorption coefficient µ and the amount of movement $θ^t$. As described above, the forward projection model 53 can be expressed using the energy function of the above-described Expression (6). Therefore, the optimization unit 62 solves the above-described Expression (6) to perform the optimization process on the forward projection model 53 and derives the absorption coefficient µ and the amount of movement $θ^t$ of the optimized forward projection model 53. In a case in which Step S134 ends, the optimization process illustrated in FIG. 10 ends, and the process proceeds to Step S106 of the image processing illustrated in FIG. 9.

In addition, the optimization process of the optimization unit 62 in Step S104 of the image processing is not limited to the above-described aspect. Hereinafter, modification examples of the optimization process will be described.

Modification Example 1 of Optimization Process

Figure 11:
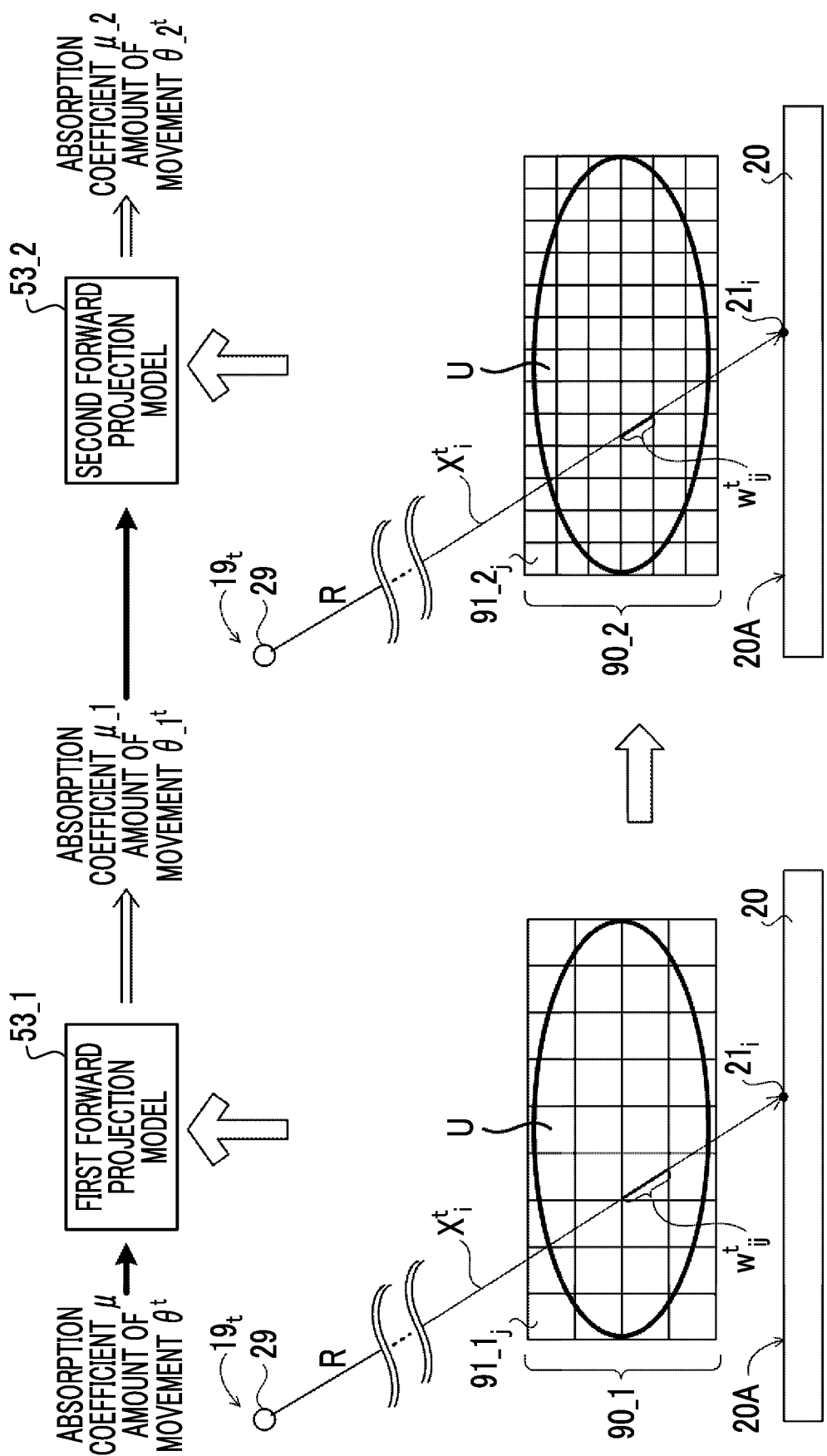
FIG. 11 is a diagram illustrating an optimization process according to a first modification example.

An optimization process according to this modification example will be described with reference to FIG. 11. In the example illustrated in FIG. 11, in first optimization, the optimization unit 62 sets a first three-dimensional model 90_1 having a voxel $91\_1_j$ with a first size as a constituent unit. The optimization unit 62 performs the optimization process on a first forward projection model 53_1, which uses the first three-dimensional model 90_1 and has a predetermined absorption coefficient μ and a predetermined amount of movement $θ^t$ as initial values, to derive an absorption coefficient μ_1 and an amount of movement θ_1$^t$.

In second optimization, the optimization unit 62 sets a second three-dimensional model 90_2 having a voxel 91_2$_j$ with a second size smaller than the size of the first voxel 91_1$_j$ as a constituent unit. The optimization unit 62 performs the optimization process on a second forward projection model 53_2, which uses the second three-dimensional model 90_2 and has the absorption coefficient μ_1 and the amount of movement θ_1$^t$ derived by the first forward projection model 53_1 as initial values, to derive an absorption coefficient μ_2 and an amount of movement θ_2$^t$.

As described above, as the optimization process, the optimization unit 62 according to this modification example repeats the optimization of the forward projection model 53 while reducing the size of the voxel 91$_j$ constituting the three-dimensional model 90. In addition, the size of the voxels 91$_j$ constituting the three-dimensional model 90 used in each optimization process can be any size. For example, the size of the voxel 91$_j$ in the last optimization process on the forward projection model 53 may be determined according to the desired resolution. In addition, the size of the voxel 91$_j$ in each optimization process may be determined from the number of times the optimization process is repeated, the processing load applied to the optimization process, and the like.

Figure 12:
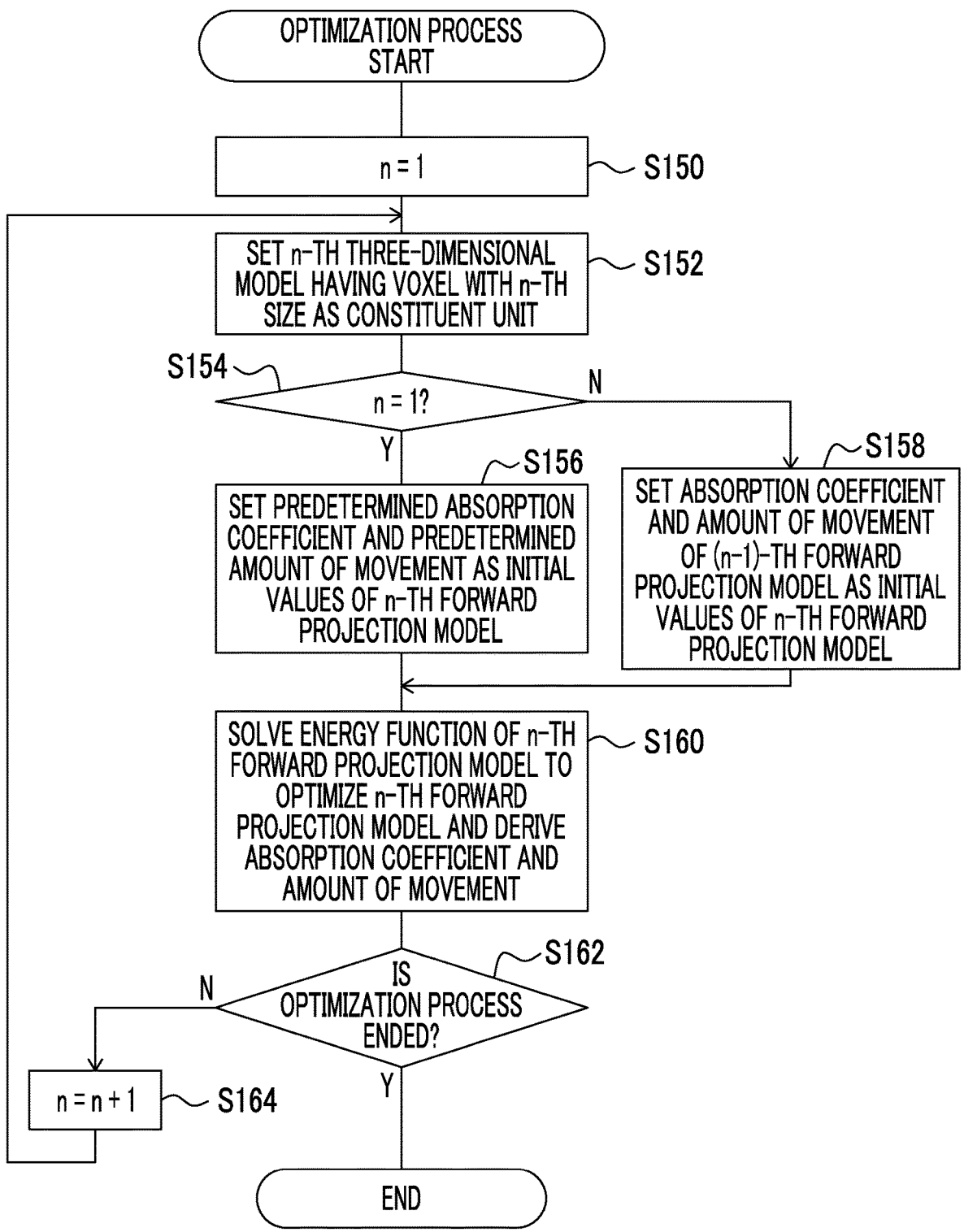
FIG. 12 is a flowchart illustrating an example of the flow of the optimization process according to the first modification example.

FIG. 12 is a flowchart illustrating an example of the flow of the optimization process in this modification example. The optimization process illustrated in FIG. 12 includes a plurality of optimization processes on the forward projection model 53.

In Step S150 of FIG. 12, the optimization unit 62 sets a variable n indicating the number of optimization processes to "1".

Then, in Step S152, the optimization unit 62 virtually sets an n-th three-dimensional model 90_n having a voxel 91_n$_j$ with an n-th size as a constituent unit in the three-dimensional space in which the object U is presumed to be present. For example, in the case of a first optimization process, n is 1, and the first three-dimensional model 90_1 having the voxel 91_1$_j$ with the first size as the constituent unit is set as illustrated in FIG. 11.

Then, in Step S154, the optimization unit 62 determines whether or not the variable *n* is "1". In other words, it is determined whether or not the optimization process performed in Step S152 is the first optimization process. In a case in which the variable n is "1", the determination result in Step S154 is "Yes", and the process proceeds to Step S156. In Step S156, the optimization unit 62 sets a predetermined absorption coefficient μ and a predetermined amount of movement θ$^t$ as the initial values of the n-th forward projection model 53_n and then proceeds to Step S160. Specifically, as described above, the optimization unit 62 sets the predetermined absorption coefficient μ and the predetermined amount of movement θ$^t$ as the initial values of the first forward projection model 53_1.

On the other hand, in Step S154, in a case in which the variable n is not 1, the determination result is "No", and the process proceeds to Step S158. In other words, in a case in which the optimization process performed in Step S152 is the second or subsequent optimization process, the process proceeds to Step S158. In Step S158, the optimization unit 62 sets an absorption coefficient μ_n−1 and an amount of movement θ_n−1$^t$ obtained by an (n−1)-th forward projection model 53_n−1 as the initial values of the n-th forward projection model 53 and then proceeds to Step S160. Specifically, in the case of the second optimization process, the variable n is "2", and the optimization unit 62 sets the absorption coefficient μ_1 and the amount of movement θ_1$^t$ as the initial values of the second forward projection model 53_2 as described above.

In Step S160, the optimization unit 62 solves the energy function of the n-th forward projection model 53_n to perform the optimization process on the forward projection model 53_n and derives an absorption coefficient μ_n and an amount of movement θ_n$^t$. As described above, the n-th forward projection model 53_n can be expressed using the energy function of the above-described Expression (6). Therefore, the optimization unit 62 solves the above-described Expression (6) to perform the optimization process on the n-th forward projection model 53_n and derives the absorption coefficient μ_n and the amount of movement θ_n$^t$ in the optimized forward projection model 53_n.

Then, in Step S162, the optimization unit 62 determines whether or not to end the optimization process illustrated in FIG. 12. In this modification example, the number of times the optimization process is repeated while reducing the size of the voxel 91$_j$ is predetermined. In other words, the maximum value of the variable n at the optimum position is predetermined. Therefore, the optimization unit 62 determines whether or not to end the optimization process on the basis of whether or not the currently set variable n is a predetermined maximum value. In a case in which the optimization process is not ended, the determination result in Step S162 is "No", and the process proceeds to Step S164.

In Step S164, the optimization unit 62 adds 1 to the variable n (n=n+1), returns to Step S152, and repeats the processes in Steps S152 to S162.

On the other hand, in a case in which the optimization process is ended, the determination result in Step S162 is "Yes", and the optimization process illustrated in FIG. 12 is ended. Then, the process proceeds to Step S106 of the image processing illustrated in FIG. 9.

As described above, the console 12 according to this modification example repeats the optimization of the forward projection model 53_n while reducing the size of the voxel 91$_j$ constituting the three-dimensional model 90 as the optimization process. In other words, after the optimization process is performed on a low-resolution forward projection model 53_n, the optimization process is performed on a high-resolution forward projection model 53_n. The size of the voxel 91$_j$ increases to reduce the number of voxels 91$_j$ constituting the three-dimensional model 90. The number of voxels 91$_j$ is reduced, and the optimization process is performed on the forward projection model 53, which makes it possible to reduce the processing time and processing load required for the optimization process. Further, the optimization process is performed on the high-resolution forward projection model 53_n using, as the initial values, the absorption coefficient μ and the amount of movement θt obtained by performing the optimization process on the low-resolution forward projection model 53_n. Therefore, it is possible to reduce the processing time and processing load required for the optimization process on the high-resolution forward projection model 53_n. Furthermore, according to this modification example, it is possible to improve the accuracy of deriving the amount of movement θ$^t$.

Modification Example 2 of Optimization Process

Figure 13:
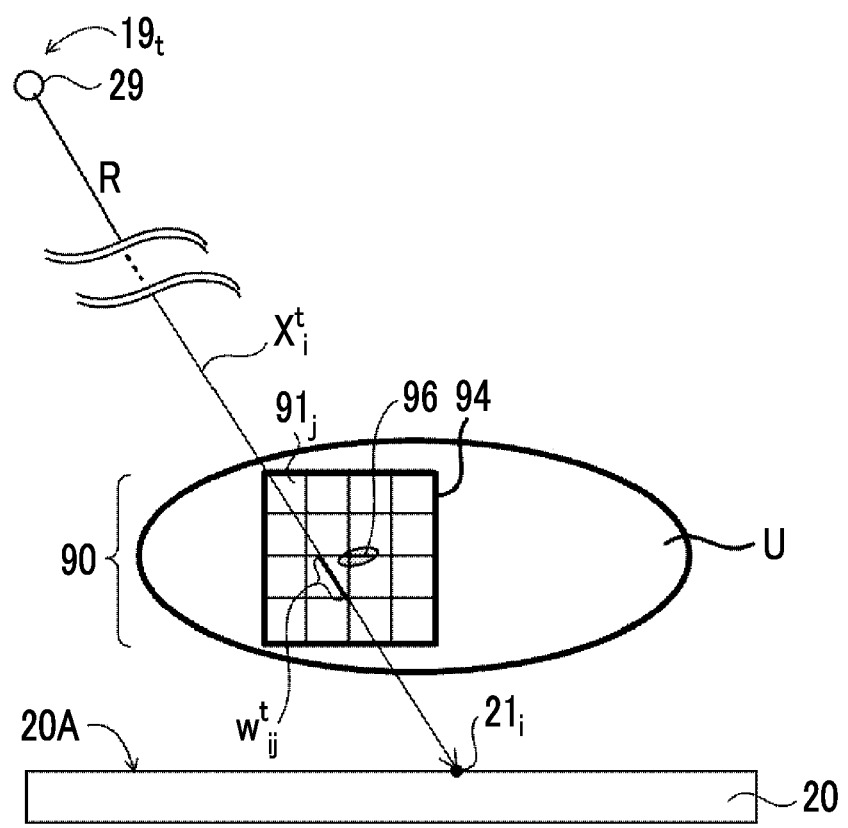
FIG. 13 is a diagram illustrating an optimization process according to a second modification example.

An optimization process according to this modification example will be described with reference to FIG. 13. The optimization unit 62 according to this modification example performs the optimization process on the forward projection model 53 using a three-dimensional model 90 that is virtually set in a three-dimensional space corresponding to a feature region 94 of the object U in the three-dimensional space in which the object U is disposed.

That is, the optimization unit 62 according to this modification example sets the three-dimensional model 90 in a portion of the three-dimensional space in which the object U is disposed. As described above, in this modification example, the feature region 94 in which the three-dimensional model 90 is provided is smaller than the region in which the three-dimensional model 90 is provided in the above-described embodiment. Therefore, it is preferable that the feature region 94 is a region including a feature structure 96. The feature structure 96 may be, for example, a structure including a feature point in a radiographic image indicating the object U. Further, the feature structure 96 may be, for example, a structure in which the feature amount of an image indicating the structure is equal to or greater than a threshold value. Specific examples of the feature structure 96 include at least one of a mammary gland or a calcification in a case in which the object U is the breast.

The optimization unit 62 according to this modification example performs the optimization process on the forward projection model 53 using the three-dimensional model 90 set for the feature region 94 to derive the amount of movement $\theta^r$. In addition, the optimization unit 62 performs the optimization process on the forward projection model 53 using the three-dimensional model 90 virtually set in the three-dimensional space in which the entire object U is present, using the derived amount of movement $\theta^r$ as the amount of movement $\theta^r$ of the entire object U, to derive the absorption coefficient $\mu$.

As described above, the optimization unit 62 according to this modification example performs the optimization process on the forward projection model 53 using the three-dimensional model 90 virtually set in the feature region 94 that includes the feature structure 96 and that is a portion of the three-dimensional space in which the object U is disposed.

Figure 14:
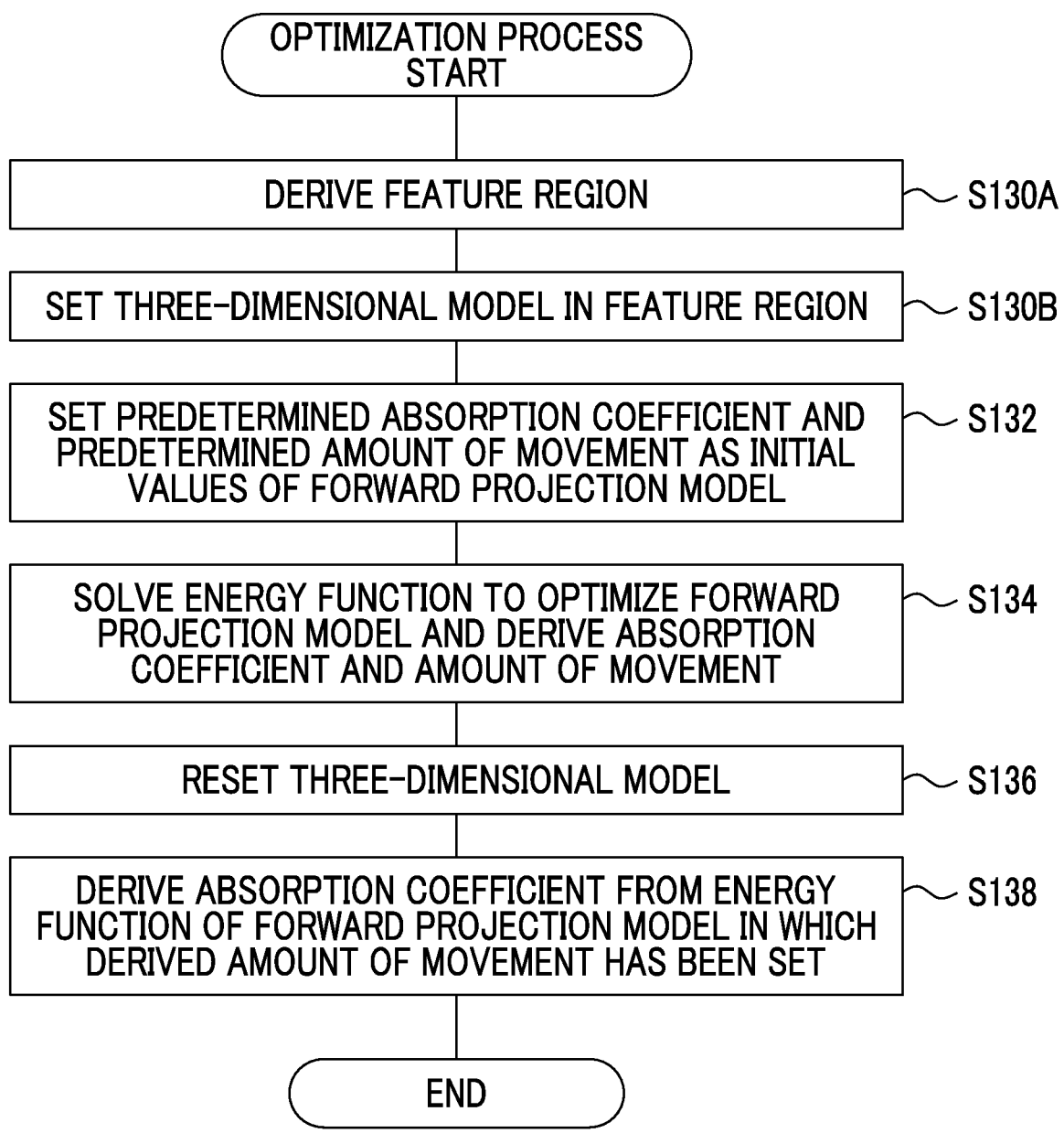
FIG. 14 is a flowchart illustrating an example of the flow of the optimization process according to the second modification example.

FIG. 14 is a flowchart illustrating an example of the flow of the optimization process according to this modification example. The optimization process illustrated in FIG. 14 differs from the above-described optimization process illustrated in FIG. 10 in that it includes processes in Steps S130A and 5130B instead of Step S130 and includes processes in Steps S136 and S138 after the process in Step S134.

In Step S130A of FIG. 14, the optimization unit 62 derives the feature region 94 in which the three-dimensional model 90 is disposed. For example, in this modification example, an image analysis or computer aided diagnosis (hereinafter, referred to as CAD) algorithm is applied to a tomographic image, which is obtained by reconstructing the projection images acquired in Step S100 of the image processing (see FIG. 9) using a back projection method, such as a filter back projection (FBP) method or an iterative reconstruction method, and which has not been subjected to movement influence correction, to specify the feature structure 96 having an image feature amount equal to or greater than a threshold value and to derive, as the feature region 94, a region with a predetermined size which includes the specified feature structure 96. A method by which the optimization unit 62 derives the feature region 94 is not particularly limited. For example, the tomographic image obtained by reconstructing the projection images as described above may be displayed on the display unit 58, and the feature structure 96 designated by the operation of the user on the displayed tomographic image through the operation unit 56 may be acquired.

Then, in Step S130B, the optimization unit 62 sets the three-dimensional model 90, which has the voxel $91_j$ with a predetermined size as a constituent unit, for the feature region 94 as described above.

Then, in Step S132, the optimization unit 62 sets a predetermined absorption coefficient $\mu$ and a predetermined amount of movement $\theta^r$ as the initial values of the forward projection model 53 as described above and then proceeds to Step S134.

Then, in Step S134, the optimization unit 62 solves the energy function of the above-described Expression (6) to optimize the forward projection model 53 as described above and derives the absorption coefficient $\mu$ and the amount of movement $\theta^r$ of the optimized forward projection model 53.

Then, in Step S136, the optimization unit 62 resets the three-dimensional model 90 having the voxel $91_j$ with a predetermined size as a constituent unit in the three-dimensional space including the region in which the object U is present.

Then, in Step S138, the optimization unit 62 performs the optimization process on the forward projection model 53 in which the amount of movement $\theta^r$ derived in the Step S134 is set. Specifically, the optimization unit 62 solves the energy function of the above-described Expression (6), using the amount of movement as $\theta^r$ and the absorption coefficient $\mu$ as a parameter, to perform the optimization process on the forward projection model 53 and derives the absorption coefficient $\mu$ and the amount of movement $\theta^r$ of the optimized forward projection model 53. In addition, the amount of movement $\theta^r$ derived here is the same as the amount of movement $\theta^r$ derived in Step S134. Further, the absorption coefficient $\mu$ derived in Step S134 may be applied as the absorption coefficient $\mu$ in the feature region 94. In a case in which Step S138 ends, the optimization process illustrated in FIG. 14 ends, and the process proceeds to Step S106 of the image processing illustrated in FIG. 9.

As described above, the console 12 according to this modification example performs the optimization process on the forward projection model 53 using the three-dimensional model 90 set in the three-dimensional space including the entire object U, using the amount of movement $\theta^r$ obtained by performing the optimization process on the forward projection model 53 using the three-dimensional model 90 set in the feature region 94 which is a portion of the three-dimensional space in which the object U is disposed. The setting of the three-dimensional model 90 in a portion of the three-dimensional space in which the object U is disposed makes it possible to reduce the number of voxels $91_j$ constituting the three-dimensional model 90. The number of voxels $91_j$ is reduced, and the optimization process is performed on the forward projection model 53, which makes it possible to reduce the processing time and processing load required for the optimization process.

As described above, the console 12 according to the above-described embodiment processes a plurality of projection images obtained by irradiating the object U with the radiation R emitted from the radiation source 29 at each of the plurality of irradiation positions $19_t$ having different irradiation angles $\alpha$. The console 12 comprises the CPU 50A. The CPU 50A acquires a plurality of projection images, performs the optimization process on the forward projection model 53, which has, as parameters, the absorption coefficient $\mu$ assigned to each voxel $91_j$ of the three-dimensional model 90 that is virtually set in the three-dimensional space in which the object U is disposed and has a plurality of voxels 91$_j$ as constitutional units, the intersection length $w^t_{ij}$ of each voxel 91$_j$ where the path $X^t_i$ of the radiation R emitted at the irradiation position 19$_t$ intersects the three-dimensional model 90, and the amount of movement $\theta^t$ of the object U, on the basis of the projection images at each of the plurality of irradiation positions 19$_t$, and generates the tomographic image of the object U using the optimized parameters.

With the above configuration, according to the console 12 of the above-described embodiment, the use of the forward projection model 53 makes it possible to suppress the influence of structures other than the structure used to correct the amount of movement $\theta^t$. Therefore, it is possible to correct the movement of the object U with high accuracy. As a result, according to the console 12 of the above-described embodiment, it is possible to obtain a high-quality tomographic image with high accuracy.

In addition, in the above-described embodiment, the aspect in which the optimization unit 62 performs, as the optimization process on the forward projection model 53, the process of bringing the pixel value of each pixel of the pseudo-projection image close to the pixel value of each pixel of the corresponding projection image without obtaining T images which are the pseudo-projection images obtained by the forward projection model 53 has been described. The method for performing the optimization process on the forward projection model 53 is not limited to this aspect. As the optimization process on the forward projection model 53, a method may be used which sequentially acquires T pseudo-projection images using the forward projection model 53 and brings the acquired T pseudo-projection images close to the corresponding T projection images.

In addition, in a case in which the amount of movement $\theta^t$ is relatively large, the optimization process on the forward projection model 53 may be insufficient, or the quality of the tomographic image generated by the forward projection model 53 may deteriorate. In some cases, the amount of movement $\theta^t$ of the breast, which is the object, is large. For example, the subject makes a large movement during the tomosynthesis imaging. In this case, for example, it is preferable to capture the projection image again. Therefore, when the amount of movement $\theta^t$ derived by performing the optimization process on the forward projection model 53 is greater than a preset threshold value, a warning may be issued.

Further, in the above-described embodiment, the aspect in which the console 12 is an example of the image processing device according to the present disclosure has been described. However, devices other than the console 12 may have the functions of the image processing device according to the present disclosure. In other words, for example, the mammography apparatus 10 or an external device other than the console 12 may have some or all of the functions of the image acquisition unit 60, the optimization unit 62, the tomographic image generation unit 64, and the display control unit 66. Further, the image processing device according to the present disclosure may be configured by a plurality of devices. For example, a device other than the console 12 may have some of the functions of the image processing device.

In addition, in the above-described embodiment, the aspect in which the breast is applied as an example of the object according to the present disclosure and the mammography apparatus 10 is applied as an example of the radiography apparatus according to the present disclosure has been described. However, the object is not limited to the breast, and the radiography apparatus is not limited to the mammography apparatus. For example, the object may be the chest, the abdomen, or the like, and radiography apparatuses other than the mammography apparatus may be applied.

In addition, in the above-described embodiment, for example, the following various processors can be used as a hardware structure of processing units performing various processes, such as the image acquisition unit 60, the optimization unit 62, the tomographic image generation unit 64, and the display control unit 66. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (programs) to function as various processing units as described above.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). In this way, various processing units are configured by using one or more of the various processors as a hardware structure.

In addition, specifically, an electric circuit (circuitry) obtained by combining circuit elements, such as semiconductor elements, can be used as the hardware structure of the various processors.

Further, in the above-described embodiment, the aspect in which the imaging program 41 is stored (installed) in the ROM 40B in advance and the image generation program 51 is stored (installed) in the ROM 50B in advance has been described. However, the present disclosure is not limited thereto. Each of the imaging program 41 and the image generation program 51 may be recorded on a recording medium, such as a compact disc read only memory (CD-ROM), a digital versatile disc read only memory (DVD-ROM), or a universal serial bus (USB) memory, and then provided. Furthermore, each of the imaging program 41 and the image generation program 51 may be downloaded from an external device through the network.

What is claimed is:

1. An image processing device that processes a plurality of projection images obtained by irradiating an object with radiation emitted from a radiation source at each of a plurality of irradiation positions having different irradiation angles, the image processing device comprising:
   at least one processor,
   wherein the processor acquires the plurality of projection images, performs an optimization process on a forward projection model, which has, as parameters, an absorption coefficient assigned to each voxel of a three-dimensional model that is virtually set in a three-dimensional space in which the object is disposed and has a plurality of voxels as constituent units, an intersection length of each voxel where a path of the radiation emitted at the irradiation position intersects the three-dimensional model, and an amount of movement of the object, on the basis of the projection images at each of the plurality of irradiation positions, and generates a tomographic image of the object using the optimized parameters.

2. The image processing device according to claim 1, wherein the processor generates the tomographic image using the absorption coefficient of the optimized forward projection model.

3. The image processing device according to claim 1, wherein, as the optimization process, the processor brings each pixel value of a plurality of pseudo-projection images obtained by performing pseudo-projection at the plurality of irradiation positions using the forward projection model close to each pixel value of the plurality of projection images.

4. The image processing device according to claim 3, wherein the processor performs the optimization process by deriving the absorption coefficient and the amount of movement for bringing the pixel values of the pseudo-projection images close to the pixel values of the plurality of projection images.

5. The image processing device according to claim 1, wherein the processor derives the amount of movement using the optimized forward projection model.

6. The image processing device according to claim 1, wherein the processor derives the amount of movement on the basis of a forward projection model using, as the three-dimensional model, a three-dimensional model that is virtually set in a three-dimensional space corresponding to a feature region of the object in the three-dimensional space in which the object is disposed and generates the tomographic image using the derived amount of movement and the forward projection model using the three-dimensional model virtually set in the three-dimensional space in which the object is disposed.

7. The image processing device according to claim 6, wherein the feature region is a region including a structure that has a feature amount equal to or greater than a threshold value.

8. The image processing device according to claim 7, wherein the object is a breast, and
the structure is at least one of a calcification or a mammary gland.

9. The image processing device according to claim 1, wherein the processor performs the optimization process on a first forward projection model using a voxel with a first size and performs the optimization process on a second forward projection model using a voxel with a second size smaller than the first size, using the absorption coefficient and the amount of movement of the optimized first forward projection model as initial values.

10. The image processing device according to claim 9, wherein the processor repeats the optimization process while reducing the size of the voxel used.

11. The image processing device according to claim 1, wherein the processor estimates the forward projection model using an energy function defined by the absorption coefficient, the intersection length, and the amount of movement.

12. A radiography system comprising:
a radiation source that generates radiation;
a radiography apparatus that performs tomosynthesis imaging which irradiates an object with the radiation emitted from the radiation source at each of a plurality of irradiation positions having different irradiation angles to capture projection images of the object at each of the irradiation positions; and
the image processing device according to claim 1.

13. An image processing method that is executed by a computer and processes a plurality of projection images obtained by irradiating an object with radiation emitted from a radiation source at each of a plurality of irradiation positions having different irradiation angles, the image processing method comprising:
acquiring the plurality of projection images;
performing an optimization process on a forward projection model, which has, as parameters, an absorption coefficient assigned to each voxel of a three-dimensional model that is virtually set in a three-dimensional space in which the object is disposed and has a plurality of voxels as constituent units, an intersection length of each voxel where a path of the radiation emitted at the irradiation position intersects the three-dimensional model, and an amount of movement of the object, on the basis of the projection images at each of the plurality of irradiation positions; and
generating a tomographic image of the object using the optimized parameters.

14. A non-transitory computer-readable storage medium storing an image processing program that processes a plurality of projection images obtained by irradiating an object with radiation emitted from a radiation source at each of a plurality of irradiation positions having different irradiation angles, the image processing program causing a computer to perform a process comprising:
acquiring the plurality of projection images;
performing an optimization process on a forward projection model, which has, as parameters, an absorption coefficient assigned to each voxel of a three-dimensional model that is virtually set in a three-dimensional space in which the object is disposed and has a plurality of voxels as constituent units, an intersection length of each voxel where a path of the radiation emitted at the irradiation position intersects the three-dimensional model, and an amount of movement of the object, on the basis of the projection images at each of the plurality of irradiation positions; and
generating a tomographic image of the object using the optimized parameters.

* * * * *